United States Patent [19]

Heine et al.

[11] 4,288,370

[45] Sep. 8, 1981

[54] HALOGENOVINYL-SUBSTITUTED TETRA-HYDROFURAN-2-ONES

[75] Inventors: Hans-Georg Heine, Krefeld; Armin Hübner, Toenisvorst; Willy Hartmann, Krefeld, all of Fed. Rep. of Germany

[73] Assignee: Bayer Aktiengesellschaft, Leverkusen, Fed. Rep. of Germany

[21] Appl. No.: 89,344

[22] Filed: Oct. 30, 1979

Related U.S. Application Data

[62] Division of Ser. No. 936,988, Aug. 25, 1978, Pat. No. 4,225,704.

[30] Foreign Application Priority Data

Sep. 10, 1977 [DE] Fed. Rep. of Germany ....... 2740849

[51] Int. Cl.³ .......................................... C07D 307/32
[52] U.S. Cl. .................................................. 260/343.6
[58] Field of Search ..................... 260/343.6; 542/441, 542/429, 401

[56] References Cited

U.S. PATENT DOCUMENTS 3,488,732  1/1970  Heiba et al. ..................... 260/343.6
4,100,362  7/1978  Stapp ............................... 260/343.6
4,102,896  7/1978  Raphael ........................... 260/343.6

FOREIGN PATENT DOCUMENTS 2630981  11/1975  Fed. Rep. of Germany .

OTHER PUBLICATIONS

Burt et al., Pestic. Sci. 1974, 5, pp. 791-799.
Itaya et al., Chem. Abst., 88: 22593q.
Mori et al., Chem. Abst., 88: 6337d.

Primary Examiner—Henry R. Jiles
Assistant Examiner—Jane T. Fan
Attorney, Agent, or Firm—Sprung, Felfe, Horn, Lynch & Kramer

[57] ABSTRACT

Halogenovinyl-substituted tetrahydrofuran-2-ones of the formula

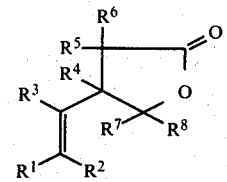

are prepared by reacting a peracid such as peracetic, perpropionic or m-chloroperbenzoic acid with a halogenvinyl-substituted cyclobutanene of the formula

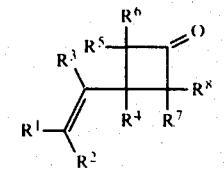

in which $R^1$ to $R^8$ can be hydrogen, halogen, cyano or various organic radicals, or in pairs can make up a ring. Products wherein $R^3$ is not hydrogen or $R^1$ is not halogen are new. The products are useful as intermediates in making insecticides.

1 Claim, No Drawings

HALOGENOVINYL-SUBSTITUTED TETRA-HYDROFURAN-2-ONES

This is a division of application Ser. No. 936,988, filed Aug. 25, 1978, now U.S. Pat. No. 4,225,704 issued at Sept. 30, 1980.

The invention relates to an unobvious process for the preparation of certain halogenovinyl-substituted tetrahydrofuran-2-ones and to certain new mono-, di- and trihalogenovinyl-substituted tetrahydrofuran-2-ones.

Halogenovinyl-substituted tetrahydrofuran-ones are valuable intermediates for the preparation of halogenovinyl-substituted cyclopropanecarboxylic acid esters, some of which are known, which are used as insecticides. Thus, in German Offenlegungsschriften (German Published Specifications) Nos. 2,623,777 and 2,630,981, a route is indicated for converting 5-($\beta,\beta$-dichlorovinyl)-4,4-dimethyltetrahydorfuran-2-one into esters of 2,2-dimethyl-3-($\beta,\beta$-dichlorovinyl)-cyclopropanecarboxylic acid. However, the processes described therein for the preparation of the lactones required for this reaction are not very economical and in addition are restricted to the synthesis of 5-vinyl-substituted tetrahydrofuran-2-ones. The interesting isomeric 4-halogenovinyl-substituted tetrahydrofuran-2-ones, of which, for example, 5,5-dimethyl-4-($\beta,\beta$-dichlorovinyl)tetrahydrofuran-2-one is known from Pestic. Sci. 1974, 792, are not producible according to the process described in DOS (German Published Specification) Nos. 2,623,777 or 2,630,981.

Furthermore, a process for the preparation of 4-halogenovinyl-substituted tetrahydrofuran-2-ones has been disclosed in German Offenlegungsschrift (German Published Specification) No. 2,702,222, in which a vinyl-substituted epoxide is subjected to a condensation reaction with a malonic acid ester in a basic medium and the 3-alkoxycarbonyl-substituted tetrahydrofuran-2-ones thereby obtained are decarbalkoxylated. The disadvantage of this process is that only tetrahydrofuran-2-ones which are dihalogenovinyl-substituted in the 4-position are producible by this means. Moreover, the tetrahydrofuran-2-ones are only producible via the corresponding 3-alkoxycarbonyl-substituted compounds, which makes this synthesis route not very economical.

The present invention now provides a process for the preparation of a halogenovinyl-substituted tetrahydrofuran-2-one of the general formula

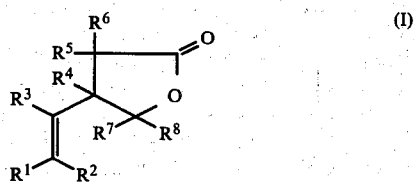

in which $R^1$, $R^2$, $R^3$ and $R^5$, which need not be identical, each represents hydrogen, chlorine, bromine, fluorine, cyano, optionally substituted alkyl, optionally substituted alkenyl, optionally substituted cycloalkyl, aryl or aralkyl and $R^4$, $R^6$, $R^7$ and $R^8$, which need not be identical, each represents hydrogen, optionally substituted alkyl, optionally substituted alkenyl, optionally substituted cycloalkyl, aryl or cyano, or $R^1$ and $R^2$, and/or $R^3$ and $R^4$, and/or $R^5$ and $R^6$, or $R^1$ and $R^3$, and/or $R^2$ and $R^4$, and/or $R^5$ and $R^6$, or $R^1$ and $R^3$, and/or $R^4$ and $R^5$ or $R^1$ and $R^2$, and/or $R^3$ and $R^5$, and/or $R^4$ and $R^6$, and/or $R^7$ and $R^8$, with the atoms to which they are linked, are bonded via an optionally substituted ring, at least one of the radicals $R^1$, $R^2$ and $R^3$ representing fluorine, chlorine or bromine, in which a halogenovinyl-substituted cyclobutanone of the general formula

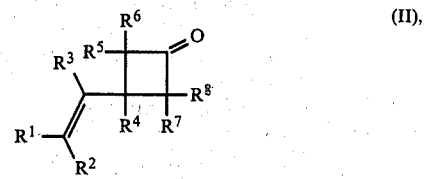

wherein $R^1$–$R^8$ have the meanings stated above, is oxidized with a peracid, optionally in the presence of a diluent.

The invention also provides, as new compounds, the halogenovinyl-substituted tetrahydrofuran-2-ones of the general formula (I), in which $R^1$, $R^2$ and $R^4$–$R^8$ have the above-mentioned meanings, but $R^3$ does not represent hydrogen.

The invention also provides, as new compounds, the halogenovinyl-substituted tetrahydrofuran-2-ones of the general formula (I), in which $R^2$–$R^8$ have the above-mentioned meanings, but $R^1$ does not represent chlorine, bromine or fluorine.

Different variants can be used for carrying out the oxidation, according the invention, of cyclobutanones of the general formula (II) with an organic peracid (see: Baeyer-Villiger-Oxydation in "Modern Synthetic Reactions" W. A. Benjamin Inc., New York (1965), page 123; "Org. Reactions", volume 9, 73 (1957); and "Molecular Rearrangements", J. Wiley Inc., New York (1963), volume 1, page 568). Thus, for example, the oxidation is advantageously carried out by the action of a peracid such as performic acid, peracetic acid, perpropionic acid, trifluoroperacetic acid, trichloroperacetic acid, monopermaleic acid, perbenzoic acid, m-chloroperbenzoic acid or monoperphthalic acid, preferably by the action of peracetic acid, perpropionic acid or m-chloroperbenzoic acid. The organic peracid can be formed in situ by the action of hydrogen peroxide on the corresponding organic acid.

The reaction can be carried out in an aqueous medium in the presence of an inert organic diluent (which term includes a solvent), for example a halogenated hydrocarbon, such as methylene chloride, chloroform, trichloroethylene, dichloroethylene or hexachlorobutadiene.

The aqueous medium can optionally be dispensed with and the reaction carried out only in an inert organic diluent.

According to the preferred embodiment of the process according to the invention, the oxidation of the cyclobutanone of the general formula (II) is carried out in a buffered medium. Buffer agents which can be used here are: alkali metal salts of organic acids, for example sodium formate, acetate, propionate, butyrate, oxalate, citrate or tartrate or potassium formate, acetate, propionate, butyrate, oxalate, citrate or tartrate, or alkali metal salts of inorganic acids, for example sodium bicarbonate or potassium bicarbonate as well as sodium carbonate or potassium carbonate. Sodium acetate in an aqueous, organic diluent and sodium bicarbonate in an organic diluent are preferred here.

The rate of the reaction in the process according to the invention depends on various factors, for example the temperature, the particular reactants employed and the solvent used. In general, the reaction takes place at about 20° C. or slightly above or below this temperature.

In order to achive optimum yields of the reaction product, in particular in the case of relatively large batches, the solution containing the organic peracid can advantageously be added dropwise to the solution containing the cyclobutanone, and the temperature can be kept at a particular value (for example 20° C.), for example by cooling. For working up, excess peracid is destroyed with a reducing agent in a manner which is in itself known and the halogenovinyl-substituted tetrahydrofuran--2-one formed is separated off by crystallization, distillation or chromatography.

Halogenovinyl-substituted cyclobutanones of the general formula (II) which can be used for carrying out the process according to the invention are known. They can be prepared by reacting a N,N-disubstituted carboxylic acid amide of the general formula $$\underset{R^8}{\overset{R^7}{\diagup}}\text{CH}-\overset{O}{\overset{\|}{C}}-\underset{R^9}{\overset{R^{10}}{\diagdown}}\text{N} \quad \text{(III),}$$

wherein

R$^7$ and R$^8$ have the above-mentioned meanings,

R$^9$ and R$^{10}$, which may be identical or different, each represent optionally substituted alkyl, cycloalkyl, alkenyl, aryl or aralkyl, or R$^9$ and R$^{10}$, with the atoms to which they are linked, form an optionally substituted ring, with an inorganic acid halide, preferably phosgene or thionyl chloride, and then reacting the product with a tertiary amine and an olefin of the general formula $$\underset{R^2}{\overset{R^1}{\diagup}}\text{C}=\underset{R^4}{\overset{R^3}{\diagdown}}\text{C}-\underset{R^6}{\overset{R^5}{\diagup}}\text{C}=\text{CH} \quad \text{(IV),}$$

wherein R$^1$–R$^6$ have the above-mentioned meanings, and a Lewis acid, and then hydrolyzing and, if appropriate, halogenating the product (see U.S. Patent Application Ser. No. 886,229).

Halogenovinyl-substituted cyclobutanones of the general formula (II) which are suitable for the reaction include 2,2-dimethyl-3-(α-methyl-β,β-dichlorovinyl)-cyclobutanone, 2,2-diethyl-3-(α,β-dichlorovinyl)-cyclobutanone, 2,2-dimethyl-3-(α,β,β-trifluorovinyl)-cyclobutanone, 2,2-dimethyl-3-(α,β-dichlorovinyl)-cyclobutanone, 2,2-dimethyl-3-(β,β-dibromovinyl)-cyclobutanone, 2,2-dimethyl-3-(α-fluoro-β, β-dichlorovinyl)-cyclobutanone, 2,2-dimethyl-3-(β-chlorovinyl)-cyclobutanone, 2,2,3-trimethyl-3-(α,β,β-trifluorovinyl)-cyclobutanone, 2,2-dimethyl-3-(β,β-difluorovinyl)-cyclobutanone, 2-ethyl-2-methyl-3-(β,β-dichlorovinyl)-cyclobutanone, 2-ethyl-2-methyl-3-(α,β,β-trichlorovinyl)-cyclobutanone, 2-ethyl-2,3-dimethyl-3-(α,β,β-trichlorovinyl)-cyclobutanone, 2,2-diethyl-3-(β,β-dibromovinyl)-cyclobutanone, 2-ethyl-2-methyl-3-(β,β-dibromovinyl)-cyclobutanone, 2-ethyl-2-methyl-3-(α-fluoro-β,β-dichlorovinyl)-cyclobutanone, 2,2-dimethyl-3-(α-ethyl-β,β-dichlorovinyl)-cyclobutanone, 2-ethyl-2,3-dimethyl-3-(β,β-dichlorovinyl)-cyclobutanone, 4-(β,β-dichlorovinyl)-spiro[3,5]-nonan-2-one, 2,2-dimethyl-3-(α,β-dibromovinyl)-cyclobutanone, 4-(α,β,β-trichlorovinyl)-spiro[3,5]-nonan-2-one, 4-(β,β-dibromovinyl)spiro[3,5]-nonan-2-one, 2,2-dimethyl-3-(β-bromo-β-chlorovinyl)-cyclobutanone, 2,2-dimethyl-4-ethyl-3-(β,β-dichlorovinyl)-cyclobutanone, 2,2,4-trimethyl-3-(α,β-dibromovinyl)-cyclobutanone, 2,2-dimethyl-4-n-butyl-3-(β,β-dichlorovinyl)-cyclobutanone and 2-methyl-3-(α,β,β-trichlorovinyl)-cyclobutanone.

Further examples are 2,2-dimethyl-3-(α-methyl-β,β-dichlorovinyl)-cyclobutanone, 2,2-diethyl-3-(α,β-dichlorovinyl)-cyclobutanone, 2,2-dimethyl-3-(α,β,β-trifluorovinyl)-cyclobutanone, 2,2-diethyl-3-(α,β,β-trichlorovinyl)-cyclobutanone, 2,2-dimethyl-3-(α,β-dichlorovinyl)-cyclobutanone, 2,2-dimethyl-3-(β,β-dibromovinyl)-cyclobutanone, 2,2-dimethyl-3-(α-fluoro-β,β-dichlorovinyl)-cyclobutanone, 2,2-dimethyl-3-(β-chlorovinyl)-cyclobutanone, 2,2,3-trimethyl-3-(α,β,β-trifluorovinyl)-cyclobutanone, 2,2-dimethyl-3-(β,β-difluorovinyl)-cyclobutanone, 2-ethyl-2-methyl-3-(β,β-dichlorovinyl)-cyclobutanone, 2-ethyl-2-methyl-3-(α,β,β-trichlorovinyl)-cyclobutanone, 2-ethyl-2,3-dimethyl-3-(α,β,β-trichlorovinyl)-cyclobutanone, 2,2-diethyl-3-(β,β-dibromovinyl)-cyclobutanone, 2-ethyl-2-methyl-3-(β,β-dibromovinyl)-cyclobutanone, 2-ethyl-2-methyl-3-(α-fluoro-β,β-dichlorovinyl)-cyclobutanone, 2,2-dimethyl-3-(α-ethyl-β,β-dichlorovinyl)-cyclobutanone, 2-ethyl-2,3-dimethyl-3-(β,β-dichlorovinyl)-cyclobutanone, 2,2-dimethyl-3-(α,β-dibromovinyl)-cyclobutanone, 2,2-dimethyl-3-(β-bromo-β-chlorovinyl)-cyclobutanone, 2,2-dimethyl-4-ethyl-3-(β,β-dichlorovinyl)-cyclobutanone, 2,2,4-trimethyl-3-(α,β-dibromovinyl)-cyclobutanone, 2,2-dimethyl-4-n-butyl-3-(β,β-dichlorovinyl)-cyclobutanone, 2-methyl-3-(α,β,β-trichlorovinyl)-cyclobutanone, 2,2-dimethyl-3-(β,β-dichlorovinyl)-cyclobutanone, 2,2-dimethyl-3-(α,β,β-trichlorovinyl)-cyclobutanone, 2,2,3-trimethyl-3-(α,β,β-trichlorovinyl)-cyclobutanone, 2,2-di-n-propyl-3-(α,β,β-trichlorovinyl)-cyclobutanone, 2,2-dimethyl-3-(α-cyano-β,β-dichlorovinyl)-cyclobutanone, 2,2-dimethyl-3-n-butyl-3-(β,β-dichlorovinyl)-cyclobutanone, 2,2-dimethyl-3-(β,β-dicyanovinyl)-cyclobutanone, 2,3-dimethyl-3-(β,β-dibromovinyl)-cyclobutanone, 2,2-dimethyl-3-(β,β-dibromovinyl)-4-n-butyl-cyclobutanone, 2,2-di-n-butyl-3-methyl-3-(α-chloro-β-cyanovinyl)-cyclobutanone, 2,2-diethyl-3-(β,β-dichlorovinyl)-4-cyclohexyl-cyclobutanone, 2,3-dimethyl-2-chloro-3-(α,β,β-trichlorovinyl)-cyclobutanone, 2-methyl-2-phenyl-3-(β,β-dichlorovinyl)-cyclobutanone, 2,2-dimethyl-3-(β-chloro-β-phenylvinyl)-cyclobutanone and 2,2-dimethyl-3-(α,β,β-trichlorovinyl)-4-benzyl-cyclobutanone, substituted by chlorine or bromine in the 4-position.

Spirocyclic cyclobutanones halogenated in the 3-position include 4-(β,β-dichlorovinyl)-spiro[5,3]nonan-2-one, 4-(α,β,β-trichlorovinyl)-spiro[5,3]nonan-2-one, 4-(β,β-dibromovinyl)-spiro[5,3]nonan-2-one, 4-(β,β-dichlorovinyl)-spiro[4,3]octan-2-one, 4-(β,β-dichlorovinyl)-3-methyl-spiro[5,3]nonan-2-one, 4-(α,β- dichlorovinyl)-spiro[5,3]nonan-2-one and 4-(α,β,β-trifluorovinyl)spiro[5,3]nonan-2-one.

The halogenovinyl-substituted tetrahydrofuran-2-ones of the general formula (I), which are readily producible by the process according to the invention, are intermediates for the preparation of insecticidal active compounds. This, for example, 4-(β,β-dichlorovinyl)-5,5-dimethyltetrahydrofuran-2-one can be smoothly opened with thionyl chloride to give 3-(β,β-dichlorovinyl)-4-chloro-4-methylvaleryl chloride, which is reacted with m-phenoxybenzyl alcohol to give the corresponding ester, which is then cyclized in the presence of a sodium alcoholate to give the insecticidally active compound 2,2-dimethyl-3-(β,β-dichlorovinyl)-cyclopropanecarboxylic acid m-phenoxybenzyl ester.

The examples which follow illustrate the process according to the invention without indicating a limitation with regard to its applicability.

EXAMPLE 1

26.0 g (0.3 mol) of sodium bicarbonate and 52.0 g (0.3 mol) of m-chloroperbenzoic acid were added to a solution of 41.8 g (0.22 mol of 2,2-dimethyl-3-(β,β-dichlorovinyl)-cyclobutanone in 500 ml of chloroform at 20° C. After standing at 20° C. for 15 hours, 10 ml of 10 percent strength aqueous sodium bisulphite solution were added and the mixture was stirred for 1 hour. The organic phase was separated off, dried over anhydrous sodium sulphate and evaporated. The crystalline residue (43.2 g) consisted solely of 4-(β,β-dichlorovinyl-5,5-dimethyltetrahydrofuran-2-one of melting point 117°–118° C. (from benzene/n-hexane).

EXAMPLE 2

(a) Preparation of the amide chloride of isobutyric acid dimethylamide.

A solution of 345.0 g (3.0 mol) of isobutyric acid dimethylamide in 2,000 ml of methylene chloride was put into a stirred vessel, which was provided with a stirrer, reflux condenser, dropping funnel and gas inlet tube, and 330.0 g (3.3 mol) of phosgene were passed in at 0° C., while cooling and stirring. The solution was allowed to warm to 20°–25° C. and, after standing overnight (15 hours), unreacted phosgene, together with about ⅓ of the methylene chloride used as the solvent, was distilled off. The residue was diluted to 2,100 ml by adding methylene chloride.

(b) Preparation of 2,2-dimethyl-3-(α,β,β-trichlorovinyl)-cyclobutanone.

50.0 g (0.5 mol) of triethylamine in 100 ml of methylene chloride was added dropwise to 350 ml of the solution, prepared according to Example 7a, of the amide chloride of isobutyric acid dimethylamide in methylene chloride at 20° C., while cooling and stirring, and the mixture was then heated and refluxed for 1 hour. Thereafter, 75.0 g (0.55 mol) of zinc chloride were added at 10° C. and 79.0 g (0.5 mol) of 1,1,2-trichlorobutadiene were added dropwise to the reaction solution in the course of 60 minutes. After heating under reflux for 5 hours, 400 ml of water were added to the reaction solution and the mixture was stirred overnight (15 hours). Separating the phases and drying the organic phase over sodium sulphate and subjecting it to fractional distillation gave 10.5 g of 1,1,2-trichlorobutadiene, 11.5 g of isobutyric acid dimethylamide and 66.8 g (59%, relative to isobutyric acid dimethylamide employed) of the ketone of boiling point 112°–117° C./10 mm Hg and refractive index $n_D^{20}$ of 1.509.

(c) 22.7 g (0.1 mol) of 2,2-dimethyl-3-(α,β,β-trichlorovinyl)-cyclobutanone, 13.0 g (0.15 mol) of sodium bicarbonate and 26.0 g (0.15 mol) of m-chloroperbenzoic acid were stirred in 300 ml of chloroform at 20° C., while cooling. After 23 hours, 10 ml of 10 percent strength aqueous sodium bisulphite solution were added and the mixture was stirred for a further 1 hour. Separating off the organic phase, washing it with saturated aqueous sodium bicarbonate solution, drying the organic phase over sodium sulphate and evaporating it gave 23.1 g of crystalline 4-(α,β, β-trichlorovinyl)-5,5-dimethyl-tetrahydrofuran-2-one of melting point 68°–70° C. (from n-hexane).

EXAMPLE 3

(a) Preparation of 2,2-dimethyl-3-(β-chlorovinyl)-cyclobutanone.

44.25 g (0.5 mol) of 1-chlorobutadiene (isomer mixture) and thereafter 50.0 g (0.5 mol) of triethylamine in 100 ml of methylene chloride were added to 350 ml of the solution, prepared according to Example 2a, of the amide chloride of isobutyric acid dimethylamide in methylene chloride at 0° C., while cooling and stirring. After warming to 20° C., 75.0 g (0.55 mol) of zinc chloride were added incrementally, while cooling, and the mixture was then heated with reflux for 6 hours. After adding 250 ml of water and customary working up, 54.2 g (68%, relative to isobutyric acid dimethylamide employed) of boiling point 81°–85° C./11–12 mm Hg and refractive index $n_D^{20}$ of 1.4759, were obtained.

(b) 63.0 g (0.75 mol) of sodium bicarbonate and 129.3 g (0.75 mol) of m-chloroperbenzoic acid were added to a solution of 79.3 g (0.5 mol) of 2,2-dimethyl-3-(β-chlorovinyl)-cyclobutanone (stereoisomer mixture) in 1,500 ml of chloroform at 20° C., while cooling and stirring. After 48 hours, 500 ml of chloroform were added. Working up as indicated in Example 2 gave 92.2 g of a yellowish oil, which was subjected to fractional distillation. 59.8 g of colorless 4-(β-chlorovinyl)-5,5-dimethyl-tetrahydrofuran-2-one (boiling point 139° C./11 mm Hg; $n_D^{20}=1.4823$) were obtained.

EXAMPLE 4

100 ml of chloroform, which contained 0.12 mol of perbenzoic acid, were added dropwise to 30.6 g (0.1 mol) of 2,2-dimethyl-3-(α,β,β-trichlorovinyl)-4-bromo-cyclobutanone (single stereoisomer) and 12.6 g (0.15 mol) of sodium bicarbonate in 200 ml of chloroform at 20° C., whil cooling. After 48 hours, the mixture was worked up as described in Example 2. 31.7 g of crystalline 3-bromo-4-(α,β,β-trichlorovinyl)-5,5-dimethyl-tetrahydrofuran-2-one of melting point 110°–111° C. (from ether/n-hexane) were obtained.

EXAMPLE 5

(a) Preparation of 3-(β,β-dichlorovinyl)-spiro[3,5]nonan-1-one 55.0 g (0.55 mol) of phosgene were passed into a solution of 77.5 g (0.5 mol) of cyclohexanecarboxylic acid dimethylamide and 300 ml of chlorobenzene at 20° C. After stirring at 30°–40° C. for 5 hours, unreacted phosgene was stripped off under reduced pressure and 55.0 g (0.55 mol) of triethylamine were then added dropwise at 20° C. The mixture was heated to 40°–50° C. for 1 hour and cooled, 75.0 g (0.55 mol) of zinc chloride were added at 20° C. and 61.5 g (0.5 mol) of 1,1-dichlorobutadiene in 50 ml of chlorobenzene were then added dropwise. After warming to 40°–50° C. for 6 hours, the mixture was worked up as described in Example 2b. Fractional distillation gave 69.6 g of crystals of melting point 58°–60° C. (from n-hexane).

(b) 4.50 g (0.05 mol) of sodium bicarbonate and 5.20 g (0.03 mol) of m-chloroperbenzoic acid were added successively to a solution of 6.66 g (0.029 mol) of 3-($\beta,\beta$-dichlorovinyl)-spiro[3,5]nonan-1-one in 200 ml of chloroform at 20° C. After stirring at 20° C. for 24 hours, the mixture was worked up as described in Example 2. Chromatography of the crystalline crude product (7.0 g) on silica gel using benzene gave 6.2 g of colorless 1-oxa-4-($\beta,\beta$-dichlorovinyl)-spiro[4,5]decan-2-one of melting point 98° C. (from ether/n-hexane).

(c) 10 ml of 30 percent strength hydrogen peroxide (0.09 mol) were added dropwise to a solution of 5.0 g (0.022 mol) of 3-($\beta,\beta$-dichlorovinyl)-spiro[3,5]nonan-1-one in 50 ml of glacial acetic acid at 20° C. After stirring at 20° C. for 24 hours, the mixture was poured onto ice and the precipitate was filtered off. 5.0 g of crystalline 1-oxa-4-($\beta,\beta$-dichlorovinyl)-spiro[4,5]decan-2-one of melting point 98° C. were obtained.

The following example illustrates the preparation of an insecticidally active compound from the lactones obtainable by the process according to the invention:

EXAMPLE 6

20.9 g (0.1 mol) of 4-($\beta,\beta$-dichlorovinyl)-5,5-dimethyl-tetrahydrofuran-2-one were dissolved in 80 ml of toluene. After adding 20 ml of thionyl chloride, the mixture was heated to the boil for 12 hours. After cooling, 22 g (0.11 mol) of 3-phenoxybenzyl alcohol were added dropwise, and 3 g of tetrabutylphosphonium chloride were added. 30 g of 50% strength potassium hydroxide solution were then added dropwise at room temperature. The mixture was subsequently stirred at room temperature for 2 hours, ice-water was added a the mixture was rendered neutral. After separating the toluene phase, the toluene was distilled off from the phase and the residue was purified on silica gel usi benzene as the running agent. A product which cc sisted of trans-2,2-dimethyl-3-(2',2'-dichloroviny cyclopropanecarboxylic acid 3-phenoxybenzyl est ($n_D^{20} = 1.5616$) to the extent of 95% was obtained.

It will be appreciated that the instant specificati and examples are set forth by way of illustration and n limitation, and that various modifications and chang may be made without departing from the spirit a: scope of the present invention.

What we claim is:

1. A halogenovinyl-substituted tetrahydrofura 2-one of the formula

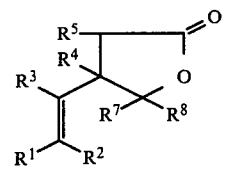

in which $R^1$ and $R^2$ each independently is hydrogen, chlorir bromine, fluorine or alkyl or 1 to 4 carbon aton $R^3$ is chlorine, bromine or fluorine, $R^4$ is hydrogen or alkyl or 1 to 4 carbon atoms, $R^5$ is hydrogen, chlorine, bromine or fluorine and $R^7$ and $R^8$ each independently is methyl or ethyl together are —(CH$_2$)$_3$—, —(CH$_2$)$_4$— or —(CF )$_5$—.

* * * * *

UNITED STATES PATENT AND TRADEMARK OFFICE
CERTIFICATE OF CORRECTION

PATENT NO. : 4,288,370
DATED : September 8, 1981
INVENTOR(S) : Hans-Georg Heine et al It is certified that error appears in the above-identified patent and that said Letters Patent are hereby corrected as shown below:

Col. 5, line 7, delete "This" and insert --Thus--.

Col. 6, line 51, delete "whil" and insert --while--.

Col. 8, line 1, delete "a" and insert --and--;

line 2, after "separating" insert --off--;

line 3, delete "tl" and insert --this--;

line 4, delete "usi" and insert --using--;

line 5, delete "cc" and insert --con--;

line 6, delete "dichloroviny" and insert --dichlorovinyl--;

line 7, delete "est" and insert --ester--;

line 10, delete "specificate" and insert --specification--;

line 11, delete "n" and insert --not--;

UNITED STATES PATENT AND TRADEMARK OFFICE
CERTIFICATE OF CORRECTION

PATENT NO. : 4,288,370
DATED : September 8, 1981
INVENTOR(S) : Hans-Georg Heine et al It is certified that error appears in the above-identified patent and that said Letters Patent are hereby corrected as shown below:

Col. 8, line 12, delete "chang" and insert --changes--;

line 13, delete "a" and insert --and--;

line 16, delete "tetrahydrofura" and insert --tetrahydrofuran--;

line 27, delete "chlorin" and insert --chlorine--;

line 29, delete "aton" and insert --atoms--;

line 34, delete "(Cr" and insert --(CH$_2$--.

Signed and Sealed this

Ninth Day of March 1982

[SEAL]

Attest:

GERALD J. MOSSINGHOFF

Attesting Officer   Commissioner of Patents and Trademarks